United States Patent
Belzer et al.

(10) Patent No.: US 10,988,509 B2
(45) Date of Patent: Apr. 27, 2021

(54) METHOD OF CULTURING AKKERMANSIA

(71) Applicant: WAGENINGEN UNIVERSITEIT, Wageningen (NL)

(72) Inventors: Clara Belzer, Wageningen (NL); Willem Meindert De Vos, Ede (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 6 days.

(21) Appl. No.: 15/572,126

(22) PCT Filed: May 4, 2016

(86) PCT No.: PCT/EP2016/060039
§ 371 (c)(1),
(2) Date: Nov. 6, 2017

(87) PCT Pub. No.: WO2016/177801
PCT Pub. Date: Nov. 10, 2016

(65) Prior Publication Data
US 2018/0094233 A1    Apr. 5, 2018

(30) Foreign Application Priority Data
May 6, 2015  (EP) ..................... 15166598

(51) Int. Cl.
| | |
|---|---|
| *C07K 14/195* | (2006.01) |
| *C12N 1/20* | (2006.01) |
| *A61P 3/08* | (2006.01) |
| *A61P 3/06* | (2006.01) |
| *A61K 38/00* | (2006.01) |

(52) U.S. Cl.
CPC ............. *C07K 14/195* (2013.01); *A61P 3/06* (2018.01); *A61P 3/08* (2018.01); *C12N 1/20* (2013.01); *A61K 38/00* (2013.01)

(58) Field of Classification Search
CPC . C07K 14/195; A61P 3/08; A61P 3/06; C12N 1/20; A61K 38/00
USPC ..................................................... 435/252.1
See application file for complete search history.

(56) References Cited

U.S. PATENT DOCUMENTS

| | | | |
|---|---|---|---|
| 6,558,926 B1 | 5/2003 | Demain et al. | |
| 2004/0265948 A1* | 12/2004 | White ..................... | C12P 33/20 435/53 |

FOREIGN PATENT DOCUMENTS

| | | |
|---|---|---|
| CN | 1856569 A | 11/2006 |
| WO | 98-054296 | 12/1998 |
| WO | 2014-075745 | 5/2014 |

OTHER PUBLICATIONS

Derrien et al., Akkermansia muciniphila gen. nov., sp. nov., a human intestinal mucin-degrading bacterium, International Journal of Systematic and Evolutionary Microbiology, 54 (2004), pp. 1469-1476.*
Lukovac et al., Differential Modulation by Akkermansia muciniphila and Faecalibacterium prausnitzii of Host Peripheral Lipid Metabolism and Histone Acetylation in Mouse Gut Organoids, vol. 5, Iss. 4 (Jul./Aug. 2014), pp. 1-10.*
Lukovac et al., Differential Modulation by Akkermansia muciniphila and Faecalibacterium prausnitzii of Host Peripheral Lipid Metabolism and Histone Acetylation in Mouse Gut Organoids, mBio, vol. 5, Issue 4, Jul./Aug. 2014, pp. 1-10.*
Kim et al, "In vitro culture conditions for maintaining a complex population of human gastrointestinal tract microbiota", J Biomed Biotechnol. 2011;2011:838040.
Caputo et al., "Whole-genome assembly of Akkermansia muciniphila sequenced directly from human stool", Biol Direct. Feb. 19, 2015;10:5.
Kwon et al., "Production of lactic acid by Lactobacillus rhamnosus with vitamin-supplemented soybean hydrolysate", Enzyme Microb Technol. 2000, 26(2-4):209-215.
Ottman et al., "Host immunostimulation and substrate utilization of the gut symbiont Akkermansia muciniphila", PhD Thesis, Wageningen University, Wageningen, Sep. 16, 2015 ISBN 978-94-6257-456-4.
Reunanen et al., "Akkermansia muciniphila Adheres to Enterocytes and Strengthens the Integrity of the Epithelial Cell Layer" Appl Environ Microbiol, 2015, 81(11):3655-62.
International search report of PCT application PCT/EP2016/060039.
Passel et al., "The Genome of Akkermansia muciniphila, a Dedicated Intestinal Mucin Degrader, and Its Use in Exploring Intestinal Metagenomes", Plos One, Mar. 3, 2011, vol. 6, No. 3, 8 pages.
"SubName: Full=Uncharacterized protein {ECO:0000313|EMBL:ACD04926.1}; Flags: Precursor", UNIPROT, XP002744586, Jul. 1, 2008, 1 page.

* cited by examiner

Primary Examiner — Jennifer M. H. Tichy
(74) Attorney, Agent, or Firm — Nixon & Vanderhye

(57) ABSTRACT

A method for cost-effectively and efficiently culturing *Akkermansia muciniphilais* is disclosed. High biomass yields can be obtained on chemically defined media. This allows for large scale production of *A. muciniphila* suitable for use in humans, such as for pharmaceutical or food applications. The *A. muciniphila* can be produced free of animal-derived products, thereby allowing a broad-range of applications.

13 Claims, No Drawings

METHOD OF CULTURING *AKKERMANSIA*

FIELD OF THE INVENTION

The present invention is in the field of culturing bacteria, in particular bacteria of the genus *Akkermansia*, particularly of the species *Akkermansia muciniphila*.

BACKGROUND OF THE INVENTION

Bacteria of the genus *Akkermansia*, particularly of the species *Akkermansia muciniphila*, are thought to play an important role in the prevention and/or treatment of metabolic disorders, such as, for example, obesity related disorders (WO2014/075745; WO2014/077246). It was found that oral administration of *A. muciniphila* to mice fed a control diet or a high-fat (HF) diet normalized diet-induced metabolic endotoxemia, adiposity and adipose tissue CD11c marker without any changes in food intake (WO2014/075745). Moreover, *A. muciniphila* treatment reduced body weight and improved body composition (i.e., fat/lean mass ratio). It was found that under HF-diet, *A. muciniphila* treatment increased mRNA expression of markers of adipocyte differentiation and lipid oxidation without affecting lipogenesis. It was also found that colonization with *A. muciniphila* completely reversed diet-induced fasting hyperglycemia, and the insulin-resistance index was similarly reduced after treatment. Finally, it has been found that *A. muciniphila* increases the intestinal barrier function (J Reunanen et al. 2015, Appl Environ Microbiol. 81:3655-62). As such, it has been suggested to use bacteria of the genus *Akkermansia*, particularly of the species *A. muciniphila*, in food or pharmaceutical applications. As such, high biomass yields of *Akkermansia* are desired.

Derrien et al. (2004, Int. J. Syst. Evol. Microbiol. 54: 1469-76) teach that *A. muciniphila* strain MucT can be isolated and grown on a basal anaerobic medium containing hog gastric mucin as the sole carbon and nitrogen source. The authors also teach that *A. muciniphila* can be grown on rich media, such as Columbia Broth (CB) and Brain Heart Infusion (BHI) broth, but with a final optical density that is half the final optical density that can be obtained with the mucin medium. All media suitable for culturing *Akkermansia* known so far contain animal components. BHI derives from animal tissue, and CB contains enzymatic digests of bovine casein, animal tissue and heart muscle. *A. muciniphila* is not easily cultured, as is illustrated by the observation that no growth was observed on the rich Wilkens-Chalgren Broth (WCB) (Derrien et al., 2004). WCB is specifically designed to grow anaerobic bacteria and contains among others enzymatic digests of bovine casein and animal gelatin.

Moreover, *A. muciniphila* has been described to be incapable of growth on basal salt medium with one of the following compounds (each 10 mM unless stated otherwise) glucose, cellobiose, lactose, galactose, xylose, fucose, rhamnose, maltose, succinate, acetate, fumarate, butyrate, lactate, casitone (0.5%), casamino acids (0.5%), tryptone (0.5%), peptone (0.5%), yeast extract (0.5%), proline, glycine, aspartate, serine, threonine, glutamate, alanine, N-acetylglucosamine, N-acetylgalactosamine (Derrien et al., 2004).

However, only when 2 g/l (0.2%) of each peptone, yeast extract, tryptone and casitone was added to the basal medium, either of the sugars N-acetylglucosamine, N-acetylgalactosamine or glucose (10 mM each) supported growth but growth was less than a quarter of that on mucin medium (Derrien et al., 2004).

In a recent study, published ten years after its original description, *A. muciniphila* was grown in basal medium with 10 g/l casitone (equals 1%), 5 mM glucose and 5 mM fucose and 1 mM threonine (Lukovac et al., 2014, MBio. 12; 5(4). pii: e01438-14. (doi: 10.1128/mBio.01438-14)). Also here the growth yield was low and approximately 4× lower than that obtained when *A. muciniphila* is grown on mucus-containing medium. Moreover, the medium contained a high concentration of casitone, which is a proteolytic degradation product of the bovine milk protein casein, and therefore is of animal origin. Finally, the medium did not only contain the cheap sugar glucose but also the sugar fucose, which is mainly found in animal derived products and is over 100 time more expensive than glucose.

Hence, it is evident that *A. muciniphila* cannot easily be cultured, and that all media and growth conditions described so far include the use of animal-derived compounds. Animal-derived products could contain contaminants of viral, prion or bacterial origin, or contain allergens, antigenic peptides or other undesired products, or may otherwise be considered unsuitable for culturing *Akkermansia* for food or pharmaceutical application in humans, for example, because they are of a non-kosher or non-halal origin. Hitherto, mucus-containing media have been found to yield the greatest amount of biomass. As mucus is only found in animals, this is a limitation to grow *A. muciniphila* and challenges the applications of this bacterium aimed to improve human or animal health as suggested in the present scientific and patent literature. Moreover, no isolates of *A. muciniphila* other than strain MucT have been described. The growth and isolation of *A. muciniphila* has been found to be challenging, as has recently been illustrated in a study where only an enrichment was obtained but not a pure culture of *A. muciniphila* in spite of significant efforts (Caputo et al 2015, Biol Direct 10: 5 (doi:10.1186/s13062-015-0041-1)) indicating that its growth is a major bottleneck.

It was an aim of the present invention to provide a composition that could be used to culture bacteria of the genus *Akkermansia* to high final optical density (high biomass yield) and/or that has reduced complexity compared to presently known compositions for culturing bacteria of the genus *Akkermansia*, and that is preferably free of animal derived products. Such culture medium would allow large scale production of *Akkermansia* suitable for use in humans, e.g., for food, feed or pharmaceutical applications.

SUMMARY OF THE INVENTION

The present invention provides for a method of culturing bacteria of the genus *Akkermansia*, particularly of the species *Akkermansia muciniphila*, said method comprising the steps of: providing a composition comprising a monosaccharide, a nitrogen-containing derivative of a monosaccharide, and an amino acid source; inoculating said composition with bacteria of the genus *Akkermansia*; and allowing said bacteria of the genus *Akkermansia* to multiply.

The nitrogen-containing derivative of a monosaccharide may be selected from N-acetyl-glucosamine (Glc-NAc) and N-acetyl-galactosamine (Gal-Nac). It is preferably Glc-NAc. The Glc-NAc may be present in an amount ranging from about 0.001 mM to about 1 M, such as from about 0.1 mM to about 500 mM, from about 0.5 mM to about 100 mM, from about 1 mM to about 75 mM, or from about 5 mM to about 50 mM.

The monosaccharide is preferably glucose. The glucose may be present in an amount ranging from about 0.001 M to about 1 M, such as from about 0.1 mM to about 500 mM, from about 0.5 mM to about 100 mM, from about 1 mM to about 75 mM, or from about 5 mM to about 50 mM.

The composition may further comprise threonine, for example in an amount ranging from about 0.01 mM to about 100 mM.

The amino acid source in the composition may be selected from a plant-based amino acid source, a microbial-based amino acid source, or a combination of alanine, glutamate, proline and serine. In a suitable embodiment, the amino acid source is a plant protein hydrolysate, such as a soy protein hydrolysate, a pea protein hydrolysate, a wheat protein hyrolysate, a rice protein hydrolysate, a cotton protein hydrolysate, and the like.

The plant protein hydrolysate may be present in an amount ranging from about 0.01 g/l to about 1 kg/l, such as from about 0.05 to about 500 g/l, from about 0.1 to about 250 g/l, from about 0.5 to about 150 g/l, from about 1 to about 100 g/l, or from about 2 to about 80 g/l.

DETAILED DESCRIPTION OF THE INVENTION

The present inventors found that *Akkermansia muciniphila* could be cultured to very high optical density in a composition comprising glucose, N-acetyl-glucosamine, and an amino acid source. The amino acid source may ideally be fully plant or microbial based.

Thus, the present disclosure also relates to a composition for culturing bacteria, particularly of the genus *Akkermansia*, specifically *Akkermansia muciniphila*, comprising a monosaccharide, a nitrogen-containing derivative of a monosaccharide, and an amino acid source.

The monosaccharide may be any monosaccharide, particularly one that is commonly used for cost-effectively culturing bacteria, and is preferably glucose.

The nitrogen-containing derivative of a monosaccharide may be selected from N-acetyl-glucosamine (Glc-NAc) and N-acetyl-galactosamine (Gal-Nac), and is preferably N-acetyl-glucosamine.

The composition may comprise the monosaccharide, such as glucose, in a concentration ranging from about 0.001 mM to about 1 M, such as from about 0.1 mM to about 500 mM, from about 0.5 mM to about 100 mM, from about 1 mM to about 75 mM, or from about 5 mM to about 50 mM.

The composition may comprise the nitrogen-containing derivative of a monosaccharide, such as Glc-NAc, in a concentration ranging from about 0.001 mM to about 1 M, such as from about 0.1 mM to about 500 mM, from about 0.5 mM to about 100 mM, from about 1 mM to about 75 mM, or from about 5 mM to about 50 mM.

The composition of this disclosure may be free of animal derived products.

The amino acid source may be any amino acid source known to the skilled person, and includes, without limitation, an amino acid source derived from an animal, derived form a plant, or derived from a microorganism. The amino acid source may be, for instance, a protein hydrolysate, such as plant-derived protein hydrolysates. Protein hydrolysates are manufactured from protein sources using (partial) hydrolysis and are typically composed of a mixture of peptides, amino acids, carbohydrates and lipids, and a multitude of unidentified components with indeterminate biological activity. They are often produced by the enzymatic, alkaline or acidic digestion of a given raw material from various sources, such as, without limitation, plant sources, e.g., soy, wheat, pea, chickpea or cotton.

The amino acid source may include commercial amino acid sources such as: yeast extracts, for example, the ultrafiltered HyPep™ YE or UltraPep™ YE, or Hy-Yest™; dairy hydrolysates, for example, derived from casein, lactalbumin and milk solid hydrolysates, such as Amicase™, Hy-Case™ Amino, Hy-Case™ SF, N-Z-Amine™ A, N-Z-Amine™ AS, N-Z-Amine™ EKG, N-Z-Case™ Plus, N-Z-Case™ TT, Edamin F, or Tryptone (the assortment of peptides formed by the digestion of casein by the protease trypsin); Plant protein hydrolysates such as HyPep 1510™ (enzymatic hydrolysate of soy), HyPep 1511™ (ultrafiltered enzymatic digest of soy), HyPep 1512™ (enzymatic digest of soy), HyPep 4601N™ (ultrafiltered enzymatic digest of wheat gluten), HyPep 5603™ (ultrafiltered enzymatic digest of rice protein and wheat gluten), HyPep 7504™ (ultrafiltered enzymatic digest of cotton protein), UltraPep Cotton™, Amisoy (an acid digest of soy isolate, resulting in a mix of amino acids and small peptides but without tryptophan), Phytone or Soytone Peptones (Difco™ and BBL brand peptones) or UltraPep Soy™. The amino acid source may also be an amino acid composition comprising an individual amino acid or a combination of individual amino acids. In a suitable embodiment, the amino acid source is a plant based amino acid source.

The amino acid source may be comprised in the composition of the invention in an amount ranging from about 0.01 g/l to about 1 kg/l, such as from about 0.05 to about 500 g/l, from about 0.1 to about 250 g/l, from about 0.5 to about 150 g/l, from about 1 to about 100 g/l, or from about 2 to about 80 g/l. For example, HySoy or Amisoy may be incorporated in the composition taught herein in an amount ranging from about 0.01 g/l to about 1 kg/l, such as from about 0.05 to about 500 g/l, from about 0.1 to about 250 g/l, from about 0.5 to about 150 g/l, from about 1 to about 100 g/l, or from about 2 to about 80 g/l.

Preferably, the composition of the invention comprises threonine, such as in an amount of about 0.01 to about 100 mM, preferably about 0.05 to about 50 mM, even more preferably about 0.1 to about 25 mM, yet more preferably about 0.5 to about 15 mM, more preferably about 1 to about 10 mM, such as about 1 to about 8 mM. The threonine may be present in the form of L-threonine or D,L-threonine.

In addition, the composition of the invention may comprise alanine, glutamate, proline and serine, preferably each in an amount of about 0.01 to about 100 mM, preferably about 0.05 to about 50 mM, even more preferably about 0.1 to about 25 mM, yet more preferably about 0.5 to about 15 mM, more preferably about 1 to about 10 mM, such as about 1 to about 8 mM.

In an embodiment, the composition as taught herein further comprises a buffer system to maintain the pH in the range of 5.5-8.0, preferably of 6.0-7.0, more preferably around pH 6.6. The skilled person is capable of selecting a buffer system suitable for this purpose.

In an embodiment, the composition as taught herein further comprises from about 0.1 to about 2%, such as from about 0.3 to about 1.5%, or from about 0.5 to about 1.3%, or around about 1.0% cysteine.

Although not required, vitamins may be added to the composition taught herein. Suitable vitamins that may be included, encompass, without limitation, biotin, cobalamin, PABA, folic acid, pyridoxamine, and the like. For instance, cobalamin can be employed when propionate is required as metabolic end-product instead of succinate, via the cobalamin-dependent methyl malonyl CoA mutase.

The present invention also provides a method for culturing bacteria of the genus *Akkermansia*, particularly of the species *Akkermansia rnuniciphila*, said method comprising the steps of:

providing a composition as taught herein;

inoculating said composition with bacteria of the genus *Akkermansia*;

allowing said bacteria of the genus *Akkermansia* to multiply.

Suitable culturing conditions for *Akkermansia muciniphila* include, without limitation, a temperature in the range of 20-40° C. and a pH in the range of 5.5-8.0, with optimum growth at a temperature of about 36-38° C. and pH 6.0-7.0, preferably around pH 6.5. *Akkermansia muciniphila* is a strictly anaerobic bacterium (Derrien et al. 2004. Int J System Evol Microbiol 54:1469-1476), and as such anaerobic conditions should ideally be applied to the extent possible, and contact with air should be avoided to the extent possible. The skilled person is acquainted with anaerobic culturing methods.

The present invention is further illustrated, but not limited, by the following examples.

From the above discussion and these examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

EXAMPLES

Example 1

Growth of *A. muciniphila* is Stimulated by Glucose and N-acetylglucosamine

*A. muciniphila* Muc$^T$ (ATTC BAA-835) was grown in basal anaerobic medium as described previously (Derrien et al., 2004, supra). The medium was supplemented with purified hog mucus alone (Type III; Sigma; 0.5%), with mucus (0.25%) alone or with added sugars, or with tryptone (Difco; 1%) with added sugars. The used sugars included D-glucose (Glucose), D-fucose (Fucose), or N-acetylglucosamine (GlcNac), alone at 20 mM or in combination at 10 mM final concentration, respectively. Incubations with sugars also contained 1 mM D,L threonine (Threonine). All incubations were carried out in serum bottles sealed with butyl-rubber stoppers at 37° C. under anaerobic conditions provided by a gas phase of 182 kPa (1.8 atm) N2/CO2. Growth was determined spectrophotometrically as optical density at 600 nm (OD600) and the results are shown in Table A. In addition, HPLC analysis was used as described previously (Derrien et al., 2004, supra; Luzovac et al., 2014, supra) to determine the concentration of the indicated sugars as well as the products, including acetate, propionate, 1,2-propanediol.

TABLE A

Growth of *A. muciniphila* on various substrates. The compounds added to the basal medium are indicated with their concentrations (dimensions in between brackets) as is the OD600, which is determined after 24-60 h of incubation. Entries are from repeated experiments and varied up to approximately 25% between experiments. For abbreviations see text. The different sets of experiments are spaced for clarity.

| Glucose (mM) | Fucose (mM) | GlcNac (mM) | Tryptone (g/l) | Mucus (g/l) | Growth OD600 |
|---|---|---|---|---|---|
| — | — | — | — | 5 | 2.5 |
| — | — | — | — | 2.5 | 0.8 |
| — | — | — | — | 1.25 | 0.4 |
| 20 | — | — | — | 2.5 | 2.3 |
| — | 20 | — | — | 2.5 | 1.6 |
| — | — | 20 | — | 2.5 | 2.3 |
| 20 | — | — | 10 | — | 0.6 |
| — | 20 | — | 10 | — | 0.15 |
| — | — | 20 | 10 | — | 1.0 |
| 10 | 10 | — | 10 | — | 0.4 |
| 10 | — | 10 | 10 | — | 1.0 |

The results confirmed earlier observations (Derrien et al., 2004, supra) that 5 g/l mucus sustains good growth of *A. muciniphila* with a relatively high growth rate (generation time of approximately 2 hours) and high end OD600 of 2.5, representing approximately 5.10$^9$ cells per ml. However, reducing the mucus concentration drastically affects the growth of *A. muciniphila*. Combinations of glucose and other sugars were tested to investigate growth of *A. muciniphila*. Interestingly, glucose or N-acetylglucosamine, but not so much fucose, can compensate for a two-fold reduction of the mucus concentration to sustain growth of *A. muciniphila* to OD600 above 2.0. Moreover, from the single sugars notably N-acetylglucosamine and, to a lesser extent, glucose but not fucose could sustain growth of *A. muciniphila* in the presence of an additional nitrogen source, in this case tryptone, a tryptic digest of casein. Similar results were obtained with casitone, a pancreatic enzyme digest of casein. However, growth was several-fold reduced as compared to growth on basal medium containing 0.5% mucus, similar to what has been reported previously (Derrien et al., 2004, supra).

From the described results, one may conclude that N-acetylglucosamine would be the best sugar to sustain growth of *A. muciniphila*; however, in view of the scarcity and costs of this sugar, it would be more advantageous to use glucose. It was surprisingly found that by combining glucose with N-acetylglucosamine, the growth of *A. muciniphila* was much better than on glucose only (Table A).

Example 2

Growth of *A. muciniphila* is Stimulated by Threonine

While for growth of *A. muciniphila* on glucose, N-acetylglucosamine could be used to increase final optical density, an external protein source was found to be essential to sustain good growth. Remarkably, increasing concentrations of tryptone significantly stimulated the growth of *A. muciniphila*, up to a level that exceeded the level of growth that could be obtained on mucus-containing media (Table B). An amount of 32 g/l of tryptone was feasible and similar in protein concentration as normal bovine milk.

The experiment was carried out essentially as set forth in Example 1.

Additionally, the effect of increasing the concentration of threonine in a basal medium with glucose and N-acetylglucosamine was tested. Surprisingly, a considerable effect was observed with concentrations of threonine above 2 mM and preferably above 4 mM, resulting in a very high OD600 of *A. muciniphila* above 7.0, which is reaching industrial scale levels.

Interestingly, both L-threonine and D,L-threonine could be used. As D,L-threonine is more readily available and less costly, addition of D,L-threonine to the medium of the invention is preferred.

TABLE B

Growth of *A. muciniphila* on various substrates, optionally including threonine.

| Glucose (mM) | GlcNac (mM) | Threonine (mM) | Tryptone g/l | Growth OD600 |
| --- | --- | --- | --- | --- |
| 12.5 | 12.5 | 0 | 8 | 0.2 |
| 12.5 | 12.5 | 0 | 16 | 0.5 |
| 12.5 | 12.5 | 0 | 32 | 3.5 |
| 25 | 25 | 0 | 32 | 4.0 |
| 25 | 25 | 1 | 32 | 5.6 |
| 25 | 25 | 2 | 32 | 7.1 |
| 25 | 25 | 4 | 32 | 7.2 |

Example 3

Growth of *A. muciniphila* in Non-Animal Derived and Synthetic Media

Since casein is an animal-derived protein source, it was tested whether plant-based or microbe-based protein sources could be used to support growth of *A. muciniphila*. Since soy is one of the most abundant and complete protein sources, a number of commercial hydrolyzed soy preparations were tested. Good growth of *A. muciniphila* was observed on basal media with glucose and N-acetylglucosamine with HySoy and AmiSoy, both obtained from Quest International, previously found to sustain growth of pathogenic bacteria (see U.S. Pat. No. 6,558,926 and WO 1998054296). However, in all cases the addition of threonine supported growth as is shown in Table C. Highly efficient growth of *A. muciniphila* was obtained with 2 mM and even better growth with 4 mM threonine in the presence of 16 g/l HySoy.

Changing the ratio of glucose and N-acetylglucosamine in the presence of HySoy and threonine affected the growth of *A. muciniphila* and showed that also on this soy-based media both sugars are needed but the ratio may differ (Table C). This was also observed on casein-derived tryptone and indicates that optimizing the ratio of glucose and N-acetylglucosamine can be done independently of the nitrogen source.

To test whether also a microbial protein source could support growth of *A. muciniphila* yeast extract (Difco) was added. Yeast extracts are usually more expensive than soy based media (Kwon et al., Enzyme Microb Technol. 2000 Feb. 1; 26(2-4):209-215.) and hence a relatively small amount of yeast extract was added to the medium that supported growth of *A. muciniphila* to OD600 of 4.4 and it was found to even increase growth of *A. muciniphila* to OD600 6.5 (Table C). This indicates that yeast extract can be used to support growth and also indicates that increasing the protein source can further increase growth of *A. muciniphila* on non-animal derived media.

Evidently, the most cost effective way to grow bacterial cells is on a synthetic medium and hence it was tested what amino acids in the soy hydrolysate could support growth. It was found that a mixture of 4 amino acids, alanine, glutamate, proline and serine (4 mM each) could support growth of *A. muciniphila* without the need for other amino acids apart from threonine in the presence of glucose and N-acetylglucosamine (Table C). The observed growth exceeded the growth on mucus alone (see above) and hence this opens the way for further optimizing the cost-effective growth of *A. muciniphila*. In fact, serine could also be replaced by threonine and a combination of only threonine and proline was found to be highly effective to act as a nitrogen source for *A. muciniphila*.

TABLE C

Growth of *A. muciniphila* on various substrates and HySoy and yeast extract (YE) at 10 g/l and 4 amino acids (AA), consisting of alanine, glutamate, proline and serine (4 mM each). The experiments were performed essentially as described in Example 5.

| Glucose (mM) | GlcNac (mM) | Threonine (mM) | HySoy (g/l) | Additions | Growth OD600 |
| --- | --- | --- | --- | --- | --- |
| 25 | 25 | 0 | 16 | — | 0.2 |
| 25 | 25 | 2 | 16 | — | 1.8 |
| 25 | 25 | 4 | 16 | — | 4.4 |
| 50 | 0 | 2 | 16 | — | 0.1 |
| 0 | 50 | 2 | 16 | — | 3.9 |
| 40 | 10 | 2 | 16 | — | 0.3 |
| 10 | 40 | 2 | 16 | — | 2.8 |
| 25 | 25 | 4 | 16 | YE (10 g/l) | 6.5 |
| 25 | 25 | 4 | — | AA (4 mM) | 2.9 |

Example 4

Industrial Scale Fermentation of *A. muciniphila*

To illustrate the capacity to produce *A. muciniphila* at a large scale, it was grown on a basal medium as described above containing per kg 32 gram HySoy, 25 gram glucose, 4.4 gram N-acetylglucosamine, 4 gram threonine, 0.5 gram cysteine, and a vitamin solution (see Derrient et al 2004, vide supra) in a 600 liter fermentor at pH 7.0. After the fermentation the OD600 of the culture was 7.2, indicating that the medium with the glucose, N-acetyl-glucosamine and a non-animal protein source was capable of sustaining excellent growth of *A. muciniphila* at an industrial scale level.

The invention claimed is:

1. A method of culturing bacteria of the species *Akkermansia muciniphila*, said method comprising:
   inoculating a composition with bacteria of the species *Akkermansia muciniphila*, said composition comprising glucose, a nitrogen-containing derivative of a monosaccharide, threonine, and an amino acid source, said nitrogen-containing derivative of a monosaccharide selected from the group consisting of N-actetyl-glucosamine (Glc-NAc) and N-actetyl-galactosamine (Gal-NAc).

2. The method according to claim 1, wherein the nitrogen-containing derivative of a monosaccharide is Glc-NAc.

3. The method according to claim 1, wherein the nitrogen-containing derivative of a monosaccharide is Glc-NAc present in an amount ranging from about 0.001 mM to about 1 M.

4. The method according to claim 1, wherein the glucose is present in an amount ranging from about 0.001 M to about 1 M.

5. The method according to claim 1, wherein the threonine is present in an amount ranging from about 0.01 mM to about 100 mM.

6. The method according to claim 1, wherein the amino acid source is selected from a plant-based amino acid source, a microbial-based amino acid source, or a combination of alanine, glutamate, proline and serine.

7. The method according to claim 1, wherein the amino acid source is a plant protein hydrolysate.

8. The method according to claim 1, wherein the amino acid source is a plant protein hydrolysate present in an amount ranging from about 0.01 g/l to about 1 kg/l.

9. The method according to claim 1, wherein the amino acid source is a plant protein hydrolysate present in an amount ranging from about 0.05 to about 500 g/l.

10. The method according to claim 1, wherein the amino acid source is a plant protein hydrolysate present in an amount ranging from about 0.1 to about 250 g/l.

11. The method according to claim 1, wherein the amino acid source is a plant protein hydrolysate present in an amount ranging from about 0.5 to about 150 g/l.

12. The method according to claim 1, wherein the amino acid source is a plant protein hydrolysate present in an amount ranging from about 1 to about 100 g/l.

13. The method according to claim 1, wherein the amino acid source is a plant protein hydrolysate present in an amount ranging from about 2 to about 80 g/l.

\* \* \* \* \*